United States Patent [19]

Hansen et al.

[11] Patent Number: 4,921,743

[45] Date of Patent: May 1, 1990

[54] USE OF SORBENT SHEET MATERIALS AS EVAPORATIVE COOLANTS

[75] Inventors: Paul E. Hansen; Thomas I. Insley, both of Lake Elmo, Minn.; Christopher J. Libbey, St. Joseph, Wis.

[73] Assignee: Minnesota Mining and Manufacturing Company, St. Paul, Minn.

[21] Appl. No.: 387,010

[22] Filed: Jul. 31, 1989

Related U.S. Application Data

[62] Division of Ser. No. 100,914, Sep. 25, 1987.

[51] Int. Cl.⁵ .............................................. B32B 3/06
[52] U.S. Cl. ..................................... 428/102; 428/283; 428/284; 428/323; 428/327; 428/903; 428/913; 604/290; 128/156; 128/165
[58] Field of Search ..................... 128/156, 169, 165; 604/291, 290, 379, 380; 428/903, 323, 327, 913, 102, 283, 284

[56] References Cited

U.S. PATENT DOCUMENTS 4,377,160  3/1983  Romaine ............................ 128/156
4,429,001  1/1984  Holpin et al. ...................... 428/283
4,618,524  10/1986  Groitzsch et al. ................. 428/198

Primary Examiner—James J. Bell
Attorney, Agent, or Firm—Donald M. Sell; Walter N. Kirn; Philip M. Goldman

[57] ABSTRACT

A method of evaporative cooling using sorbent sheet materials comprising a fibrous web that includes entangled fibers and a solid high sorbency liquid-sorbent polymeric material is disclosed. A sorbent sheet material useful for administering cold water therapy is also described.

19 Claims, 1 Drawing Sheet

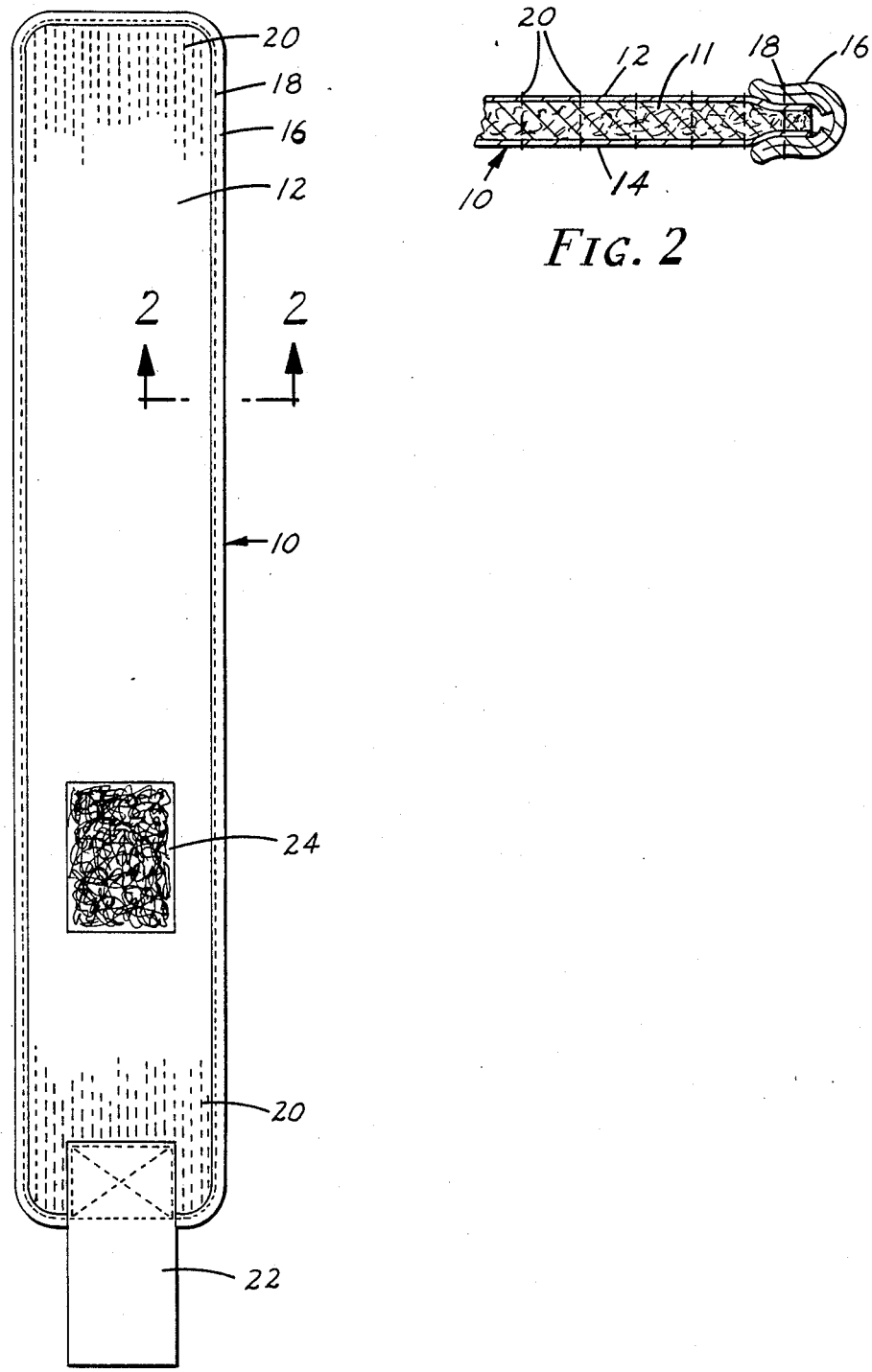

USE OF SORBENT SHEET MATERIALS AS EVAPORATIVE COOLANTS

This is a division of application Ser. No. 100,914 filed Sept. 25, 1987.

TECHNICAL FIELD

This invention relates to evaporative cooling methods and to bandages for providing evaporative cooling.

BACKGROUND OF THE INVENTION

Sorbent sheet materials are well known in the art. U.S. Pat. No. 4,429,001 describes sorbent sheet materials comprising a coherent web of entangled blown fibers prepared by extruding liquid fiber-forming material into a high velocity gaseous stream and an array of super absorbent polymeric particles dispersed within the web. European Patent Application No. 85302166.5 describes sorbent sheet products comprising a coherent web that includes entangled blown fibers and liquid transport fibers intermingled with the blown fibers and an array of solid high sorbency liquid sorbent polymeric particles uniformly dispersed and physically held within the web.

These sorbent sheet materials have been found to have a variety of uses, particularly where rapid sorption and high liquid retention are desired, such as in disposable incontinent devices, diapers, surgical swabs, bed pads and sanitary napkins.

What has not been heretofore recognized is that the ability of these materials to absorb large quantities of liquid makes them useful in devices to be used as evaporative coolants. Many materials that are currently used as evaporative coolants, such as sponges, terry cloth towels and cotton wads, absorb and hold relatively small quantities of liquid and exert a cooling effect of very limited duration.

Other materials such as that typified by the polyvinyl-alcohol gel-containing bandage disclosed in U.S. Pat. No. 4,377,160 are not as convenient as they might be since they must be manufactured in the hydrated state and are not reusable practicably.

In contrast to the above described evaporative coolants, the sorbent sheet materials described herein absorb relatively large quantities of liquid, and, therefore, exert a cooling effect for an extended period of time, and are furthermore convenient to manufacture and use since they are hydrated just prior to use and are reusable.

BRIEF SUMMARY OF THE INVENTION

The present invention provides a novel method of evaporative cooling, comprising
(a) wetting a sorbent sheet material comprising a web comprising fibers having an average diameter of about 1-20 microns and a solid high-sorbency liquid-sorbent polymeric material contained within the web with a liquid for which the polymeric material exhibits high-sorbency;
(b) placing the wetted sorbent sheet material in contact with the object to be cooled; and
(c) allowing the liquid contained in the wetted sorbent sheet material to evaporate while said wetted sorbent sheet material is in contact with the object to be cooled to provide a cooling effect on the object.

In a preferred method according to the invention, the object to be cooled is the limb of a mammal such as the leg(s) of a race horse.

The present invention further provides a novel, reusable sorbent sheet material for providing evaporative cooling, comprising
(a) a sheet comprising a web comprising fibers having an average diameter of about 1-20 microns with a solid high-sorbency liquid-sorbent polymeric material contained within the web; and
(b) water and water-vapor permeable cover sheet on each of the two exposed surfaces of the web, the cover sheets being through-bonded together through the web in an intermittent pattern over substantially the entire area of the sorbent sheet material and functioning to substantially prevent migration of the polymer from the web of the sorbent sheet material when the sorbent sheet material is wetted with a volatile liquid for which the polymeric material exhibits high-sorbency.

BRIEF DESCRIPTION OF THE DRAWINGS

In the drawings:
FIG. 1 is a top view of a bandage useful in administering cold water therapy to a mammalian limb; and
FIG. 2 is a cross-sectional view of the bandage shown in FIG. 1.

DETAILED DESCRIPTION OF THE INVENTION

By "substantially saturating" and "substantially saturated", as used in the instant specification and claims, is meant that the sorbent sheet material is caused to pick-up an amount of liquid equivalent to what would occur with complete immersion in the particular liquid employed for about five minutes.

As illustrated in FIGS. 1 and 2, the sorbent sheet material 10 of the invention comprises a web 11 formed of entangled fibers. Cover sheets 12 and 14 are situated on either side of web 11, and are through-bonded via stitch-bonding 20 over substantially the entire area of sorbent sheet material 10. Fabric edging 16 serves to prevent ravelling and is attached to sorbent sheet material 10 via stitch 18. Hook and loop fasteners 22 and 24, respectively, serve to allow attachment of the sorbent sheet material to an object such as a limb of a mammal.

Sorbent sheet materials useful in the method and bandages of the present invention and methods for manufacturing such sorbent sheet materials are described in U.S. Pat. No. 4,429,001, copending application U.S. S.N. 594,737, which was filed on Mar. 29, 1984, and is assigned to the assignee of the instant application, and copending application U.S. S.N. 91,730 which was filed on Sept. 1, 1987, and is also assigned to the assignee of the instant application, the teachings of the above patent and patent applications all being incorporated herein by reference.

The sorbent sheet material of U.S. Pat. No. 4,429,001 comprises a coherent web of entangled blown fibers prepared by extruding liquid fiber-forming material into a high-velocity gaseous stream and an array of super absorbent polymeric particles dispersed within the web.

The sorbent sheet material of said application U.S. S.N. 594,737 comprises a coherent fibrous web that includes entangled blown fibers and liquid transport fibers intermingled with the blown fibers and an array of solid high sorbency liquid-sorbent polymeric particles within the web.

The sorbent sheet material of said application U.S. S.N. 91,730 (Attorney's Docket No. F.N. 42130 USA 9A) comprises a super absorbent polymer-containing microfiber microweb incorporated into a non-woven web of blown microfibers, air-laid staple fibers or wood pulp fibers.

Melt-blown fibers are greatly preferred for sheet materials of the invention, but solution-blown fibers in which the fiber-forming material is made liquid by inclusion of a volatile solvent can be used. U.S. Pat. No. 4,011,067, which is incorporated herein by reference, describes useful apparatus and procedures for preparing a web of such fibers. However, in preparing sheet materials of this invention, fiber-forming material is generally extruded through a plurality of adjacent orifices rather than the single orifice shown in U.S. Pat. No. 4,011,067.

The sorbent particles and staple fibers, when used, are preferably introduced into the fiber stream at a point where the blown fibers have solidified sufficiently that the blown fibers will form only a point contact with both the sorbent particles and staple fibers. However, the sorbent particles and staple fibers can be mixed with the melt blown fibers under conditions that will produce an area contact with the sorbent particles and staple fibers.

The blown fibers are preferably microfibers, averaging less than about 10 micrometers in diameter, since such fibers offer more points of contact with the particles per unit volume of fiber. Very small fibers, averaging less than 5 or even 1 micrometer in diameter, may be used, especially with sorbent particles of very small size. Solution-blown fibers have the advantage that they may be made in very fine diameters, including less than one micrometer.

Blown fiber webs are characterized by an extreme entanglement of the fibers, which provides coherency and strength to a web and also adapts the web to contain and retain particulate matter and staple fibers. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end. Despite such entanglement, a sheet product may expand greatly in size during sorption.

The fibers may be formed from a wide variety of fiber-forming materials. Representative polymers for forming melt-blown fibers include polypropylene, polyethylene, polyethylene terephthalate and polyamides. Representative polymers for forming solution-blown fibers include polymers and copolymers of vinyl acetate, vinyl chloride and vinylidene chloride. Inorganic materials also form useful fibers. Fibers of different fiber-forming materials may be used in the same sheet product, either in a mixture in one layer or in different layers.

Many of the fiber-forming materials form hydrophobic fibers which can be undesirable in water sorbing sheet products. To improve the sorbent sheet material of the invention for water sorption, a surfactant in powder or liquid form may be introduced into the web of the sorbent sheet material, as by mixing powders with the sorbent particles before they are introduced into the web or spraying liquids onto the web after it is formed. Useful surfactants, which typically comprise molecules having oleophilic and hydrophilic moieties, include dioctyl ester of sodium sulfosuccinate and alkylaryl polyether alcohols. A small amount of the surfactant is generally used, such as about 0.5 to 3 weight percent of the web of the sorbent sheet material when the surfactant is applied topically. Greater amounts of surfactant may be used, however, as will be known by those skilled in the art.

The sorbent polymer is desirably included in the sorbent sheet materials of the invention to increase water pick-up and retention. Higher retention is desirable to provide resistance to pressure-induced desorption of the sheet material. The sorbent polymer further provides a metered rate of evaporative cooling.

The sorbent polymer used is generally in the form of super absorbent particles which rapidly absorb and retain large quantities of liquids. However, the sorbent polymer may also be in the form of fibers as is disclosed in U.S. Pat. No. 4,650,429, incorporated herein by reference. The preferred particles for sorbing water comprise modified starches, examples of which are described in U.S. Pat. No. 3,981,100, and high-molecular weight acrylic polymers containing hydrophilic groups. A wide variety of such water-insoluble water-sorbing particles are available commercially, and they typically sorb 20 or more times their weight of water and preferably 100 or more times their weight of water. Alkylstyrene sorbent particles (such as marketed by Dow Chemical Company under the trademark "Imbiber Beads") are useful for sorbing liquids other than water such as alcohol (e.g., isopropanol). They tend to sorb 5 to 10 times or more their weight of such liquids. In general, the sorbent particles should sorb at least their own weight of liquid whether the liquid be water or something other than water.

The sorbent particles may vary in size, at least from 50 to 3000 micrometers in average diameter. Preferably, the particles are between 75 and 1500 micrometers in average diameter.

The amount of sorbent material included in the web of the sorbent sheet material will involve balancing the amount of sorbency desired with other properties, such as integrity or strength of the web, or desired web thickness. Preferably, sorbent polymer accounts for about 1 to 50 percent by weight of the entangled fibers, and more preferably accounts for about 5 to 30 percent by weight of the entangled fibers. Most preferably, the level of sorbent polymer is such that, when the web is hydrated, the amount of sorbent polymer employed is not so great as to allow gel-blocking (i.e., the formation of a gel which is such that the void volume of the coherent web is not completely filled by the gel). Avoidance of gel-blocking is preferred so as to assure maximum pick-up of liquid if so desired, and to provide discrete evaporative sites which results in maximization of surface area and thereby enhances the rate of the evaporative cooling phenomenon.

Staple fibers may be included to act as liquid transport fibers. The transport fibers used in the web of the sorbent sheet material are generally absorbent staple fibers which rapidly absorb and wick the fluid being absorbed. Fibers useful as transport fibers are those having a water retention value of at least about 10%, preferably about 20%, and more preferably about 25% when tested according to ASTM Test Method D2402. Fibers having such a water retention value have been found to provide a desired transport of liquid into the interior of the web. Such fibers include rayon, cotton, wool and silk. A particular preferred fiber is "Absorbit" rayon fiber supplied by American Enka Company.

The size of the transport fibers is preferably in the range of about 1 to 50 denier, more preferably about 1 to 30 denier. Use of transport fibers of lower denier provide a softer hand and better mechanical hold of the sorbent particles. When using equipment such as a lickerin roll to dissociate the transport fiber during production of the product, the fibers should average between 2 to 15 centimeters in length. Preferably, the transport fibers are less than about 7 to 10 centimeters in length.

Resilient staple fibers may be included in the web of the sorbent sheet material to add bulk and conformability to the web. Many different synthetic crimped bulking fibers may be used. Polyester crimped staple fibers are readily available. Other useful fibers include acrylics, polyolefins, polyamides, etc. U.S. Pat. No. 4,118,531, which is incorporated herein by reference, describes webs of blended microfibers and crimped bulking fibers.

When staple fibers are included in the web of the sorbent sheet material, the amount of staple fibers used will depend on the amount and type of sorbent particles included in the sheet product and on the desired bulk/resiliency characteristics. Preferably, at least 25 $g/m^2$ of staple fibers per 100 $g/m^2$ of blown fibers will be used to provide sufficient transport and wicking or resiliency and bulk. Preferably, the amount of staple fiber will not exceed about 100 $g/m^2$ per 100 $g/m^2$ of the blown fibers to maintain the strength and integrity of the blown fiber matrix. Generally, greater amounts of staple fiber may be used when the denier of the fiber is higher. Most preferably, the sheet product will contain about 20 to 60 $g/m^2$ of staple fibers per 100 $g/m^2$ of the blown fiber.

Inclusion of a preservative in the web may be desired to limit microbial growth.

Cover sheets which may be used in the sorbent sheet material of the invention should be permeable to water and water vapor, and should further substantially prevent the migration of the sorbent polymer from the hydrated web when the sorbent sheet material is in use. Suitable cover sheets which may be used include "Sontara" spun lace style #8807 (available from E. I. duPont de Nemours and Company). The cover sheets are attached to one another through the intervening web by through-bonding. By "through-bonding" as used in the instant specification and claims is meant mechanical attachment of the cover sheets through the intervening web such as by stitchbonding, sewing, sonic welding or thermal sealing. Through-bonding is preferably performed in an intermittent pattern over substantially the entire area of the sorbent sheet material. The preferred intermittent pattern is a regular pattern. Preferred through-bonding is accomplished by stitch-bonding. Mechanical attachment of the cover webs to the coherent web via through-bonding provides durable bonding, prevents delamination, and allows swelling of the web within desired limits in the saturated wet stage. Because of these qualities, the sorbent sheet material is conveniently reusable.

In practicing the method of the invention, it is preferred that the sorbent material be saturated by immersion in the liquid being employed for several minutes to assure saturation of the sheet material with the liquid.

The invention will be further illustrated by the following non-limiting examples.

EXAMPLE 1

A coherent web useful in a bandage for administering cold water therapy to a horse was constructed in accordance with procedures described in said copending application U.S. S.N. 594,737 as follows. Coherent web material was prepared from polypropylene pellets ("34 MF" available commercially from Exxon Corporation) with sorbent particles ("J-550" available commercially from Grain Processing Corp., Muscatine, Iowa) and 15 denier polyethylene terephthalate staple fibers. The coherent web material contained 124 $g/m^2$ polypropylene microfibers, 17 $g/m^2$ sorbent particles, 124 $g/m^2$ staple fibers of 1.0 percent by weight of the polypropylene microfibers and "Triton X100" (a surfactant available commercially from Rohm and Haas Company). A composite structure as shown in FIG. 1 was obtained by stitchbonding two layers of the coherent web material between "Sontara #8807" cover sheets (available commercially from E. I. duPont de Nemours and Company). The stitchbonding was done on a commercially available "Arachne" machine (available commercially from Strosimport of Czechoslovakia; available domestically from Omintex of Charlotte, N.C.) as follows. A 100 denier texturized polyester yarn was used. Some of the composites were stitched with a 1:1 needle set in a plain stitch having a 5 mm spacing. Other composites were stitched with a 1:3 needle set in a chain stitch 10 mm apart. The composite was cut into a bandage 12" by 24" and hemmed around the edge to prevent ravelling. Three hook and loop fasteners (available commercially from the 3M Company under the tradename "Scotchmate ®") were attached to the top side.

EXAMPLES 2-5

A series of sorbent sheet materials in which the type and/or amount of sorbent particles was varied was prepared according to the procedures of Example 1 (including use of surfactant) using the materials indicated in TABLE 1 in the amounts indicated (expressed as $g/m^2$).

TABLE 1

| EX-AMPLE NO. | SORBENT TYPE | AMOUNT OF SORBENT PARTICLES | AMOUNT OF POLYPROPYLENE MICROFIBERS[c] | AMOUNT OF STAPLE FIBERS[d] |
|---|---|---|---|---|
| 2 | "J-400"[a] | 25 | 124 | 124 |
| 3 | "SAB 922"[b] | 20 | 124 | 124 |
| 4 | "SAB 922"[b] | 30 | 124 | 124 |
| 5 | "SAB 922"[b] | 60 | 124 | 124 |

[a]"J-400" is available commercially from Grain Processing Corp.
[b]"SAB 922" is available commercially from Stockhausen Inc., Greensboro, NC.
[c]"34 MF" polypropylene pellets available commercially from Exxon Corporation.
[d]15 denier polyethylene terephthalate staple fibers ("Kodel 431" available commercially from Eastman Chemical Company).

The above sheet materials were converted to bandages using the procedures described in Example 1.

EXAMPLE 6

A sorbent sheet material was prepared as follows utilizing the procedures of Example 9 of said copending application U.S. S.N. 91,730.

A sorbent loaded source web was prepared from polypropylene pellets "34 MF" (available from Exxon Corporation) and "SAB 922" sorbent particles (available from Stockhausen, Inc.) The web contained 124 $g/m^2$ polypropylene microfibers, 60 $g/m^2$ sorbent particles and 3 percent by weight of "Triton X100". The sorbent loaded web was then torn into discrete microfiber microweb bundles by a lickerin roll, and the bundles were loaded into a freshly generated polypropylene ("34 MF" available from Exxon Corporation) microfiber web along with 15 denier polyethylene terephthalate staple fibers ("Kodel 431" available from Eastman Chemical Company). The freshly generated web was aerosol sprayed with "Triton X100" at 3 weight percent. The resulting sheet material contained 124 g/m$^2$ polypropylene microfibers, 124 g/m$^2$ staple fibers, and 92 g/m$^2$ of microweb bundles which yielded 30g/m$^2$ of sorbent particles.

Composites of the above sheet material were made using the method described in Example 1.

EXAMPLE 7

A sheet material was made according to the method described in Example 6 but no staple fibers were used. The sheet material contained 124 g/m$^2$ polypropylene microfibers and 92 g/m$^2$ microweb bundles which resulted in 30 g/m$^2$ of sorbent particles being contained. Composites were made using the method described in Example 1.

EXAMPLE 8

A sorbent sheet material was prepared as follows, utilizing the procedures of Example 17 of said copending application U.S. S.N. 91,730.

A sorbent loaded sorce web was prepared from polypropylene microfibers and "SAB 922" sorbent particles (available from Stockhausen, Inc.) The web contained 124 g/m$^2$ polypropylene microfibers, 60 g/m$^2$ "SAB 922" and 3 percent by weight of the polypropylene microfibers of "Triton X-100". This source web along with 15 denier polypropylene terephthalate staple fibers and 4.5 denier MELTY®, (a bicomponent sheath core binder fiber available commercially from Unikika Ltd., Osaka, Japan) was introduced into a Rando Webber® air-laying apparatus (available from Rando Corporation). The lickerin devellicated the source web to form microfiber microweb bundles. The freshly generated web was aerosol sprayed with Triton X-100 at 3 weight percent. The resulting sheet material contained 54 g/m$^2$ polyethylene terephthalate, 64 g/m$^2$ MELTY® and 108 g/m$^2$ of microweb bundles which resulted in 35 g/m$^2$ of SAB 922 sorbent particles being contained.

EXAMPLE 9

A sheet material was made according to the method of Example 8, but the amount of microweb bundles was increased. The sheet material contained 54 g/m$^2$ polyethlene terephthalate, 64 g/m$^2$ MELTY® and 215 g/m$^2$ microweb bundles which resulted in 70 g/m$^2$ "SAB 922" being contained.

What is claimed is:

1. A reusable, sorbent sheet material for providing evaporative cooling, comprising
   (a) a sheet comprising a web comprising fibers having an average diameter of about 1-20 microns with a solid high-sorbency liquid-sorbent polymeric material contained within said web; and
   (b) a water and water-vapor permeable cover sheet on each of the two exposed surfaces of said web, said cover sheets being through-bonded together through said web in an intermittent pattern over substantially the entire area of said sorbent sheet material and functioning to substantially prevent migration of said polymer from said web of said sorbent sheet material when said sorbent sheet material is wetted with a volatile liquid for which said polymeric material exhibits high-sorbency.

2. A sorbent sheet material according to claim 1, wherein said polymeric material is in the form of particles which are uniformly dispersed within said web.

3. A sorbent sheet material according to claim 1 wherein said polymeric material is in the form of fibers.

4. A sorbent sheet material according to claim 1, wherein said fibers are blown fibers.

5. A sorbent sheet material according to claim 4, wherein said fibers are melt blown fibers.

6. A sorbent sheet material according to claim 4, wherein said sorbent sheet material further comprises staple fibers intermingled with said blown fibers.

7. A sorbent sheet material according to claim 6, wherein said staple fibers are present in an amount of aboiut 25 to 100 percent by weight of said blown fibers.

8. A sorbent sheet material according to claim 1, wherein said polymeric material is present in an amount of about 1 to 50 percent by weight of said fibers.

9. A sorbent sheet material according to claim 1, wherein said polymeric material is present in an amount of about 5 to 30 percent by weight of said fibers.

10. A sorbent sheet material according to claim 9, wherein the amount of said polymeric material present is insufficient to allow gel-blocking of said sorbent sheet material when wetted with said liquid.

11. A sorbent sheet material according to claim 1, wherein said fibers comprise microfibers averaging less than about 10 microns in diameter.

12. A sorbent sheet material according to claim 1, wherein said sorbent sheet material further comprises surfactant dispersed within said web.

13. A sorbent sheet material according to claim 6, wherein said staple fiber is a transport fiber.

14. A sorbent sheet material according to claim 6, wherein said staple fiber is a crimped bulking fiber.

15. A sorbent sheet material according to claim 1, wherein said web comprises microfiber microwebs incorporated into a non-woven web of blown microfibers, said microwebs containing said polymeric material.

16. A sorbent sheet material according to claim 1, wherein said polymeric material exhibits high-sorbency to water.

17. A sorbent sheet material according to claim 1, wherein said cover sheets are through-bonded by stitch-bonding.

18. A sorbent sheet material according to claim 1, further comprising a mechanical fastener to attach said sorbent sheet material to the limb of a mammal to be treated with said sorbent sheet material.

19. A sorbent sheet material according to claim 1, in the form of a bandage.

* * * * *